(12) United States Patent
Popp et al.

(10) Patent No.: US 8,235,962 B2
(45) Date of Patent: Aug. 7, 2012

(54) ABSORBENT PANT GARMENTS HAVING OPTIMIZED LEG OPENING SHAPE

(75) Inventors: Robert Lee Popp, Hortonville, WI (US); Kathleen Irene Ratliff, Neenah, WI (US); Marcille Faye Ruman, Oshkosh, WI (US); Henry Louis Carbone, II, Appleton, WI (US); Matthew Lee Koele, Chilton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2695 days.

(21) Appl. No.: 10/185,418

(22) Filed: Jun. 28, 2002

(65) Prior Publication Data

US 2004/0002691 A1 Jan. 1, 2004

(51) Int. Cl.
*A61F 13/15* (2006.01)

(52) U.S. Cl. .................. 604/386; 604/393; 604/394

(58) Field of Classification Search ............ 604/385.2, 604/4–385.3, 386, 387, 389, 391, 393, 394
See application file for complete search history.

(56) References Cited

U.S. PATENT DOCUMENTS

| | | | |
|---|---|---|---|
| 4,051,854 A | 10/1977 | Aaron |
| 4,122,552 A | 10/1978 | Tedford |
| 4,145,763 A | 3/1979 | Abrams et al. |
| 4,205,679 A | 6/1980 | Repke et al. |
| 4,402,690 A | 9/1983 | Redfern |
| 4,516,975 A | 5/1985 | Mitchell |
| 4,610,680 A | 9/1986 | LaFleur |
| 4,615,695 A | 10/1986 | Cooper |
| 4,663,220 A | 5/1987 | Wisneski et al. |
| 4,847,134 A | 7/1989 | Fahrenkrug et al. |
| 4,936,840 A | 6/1990 | Proxmire |
| 4,940,464 A | 7/1990 | Van Gompel et al. |
| 5,062,839 A | 11/1991 | Anderson |
| 5,087,253 A | 2/1992 | Cooper |
| 5,226,992 A | 7/1993 | Morman |
| 5,370,634 A | 12/1994 | Ando et al. |
| 5,399,219 A | 3/1995 | Roessler et al. |
| 5,496,298 A | 3/1996 | Kuepper et al. |
| 5,624,429 A | 4/1997 | Long et al. |
| 5,669,897 A | 9/1997 | Lavon et al. |

(Continued)

FOREIGN PATENT DOCUMENTS

EP 0 217 032 4/1987

(Continued)

*Primary Examiner* — Lynne Anderson
(74) *Attorney, Agent, or Firm* — Dority & Manning, P.A.

(57) ABSTRACT

An absorbent pant garment having a leg opening shape and fastener placement that, together, minimize the likelihood of fastener pop-opens during use. The garment includes a pair of front and back side panels on opposite transverse sides of the garment, with a refastenable seam formed between the front and back side panels including a fastening component on the front side panel and a mating fastening component on the back side panel, with elasticity in the front and/or back side panel. Each of the front and back side panels includes a waist end edge and a leg end edge, with a portion of the waist end edge and a portion of the leg end edge substantially parallel to one another adjacent a distal edge for a distance greater than a transverse width of the fastening component or mating fastening component bonded thereto. These parallel portions of the side panel edges space the fastening components and mating fastening components away from major stress points of the garment, thereby reducing the likelihood of fastener pop-opens.

76 Claims, 5 Drawing Sheets

U.S. PATENT DOCUMENTS

| | | | |
|---|---|---|---|
| 5,749,866 A | 5/1998 | Roe et al. | |
| 5,759,181 A | 6/1998 | Sayama et al. | |
| 5,830,206 A | 11/1998 | Larsson | |
| 5,855,574 A | 1/1999 | Kling et al. | |
| 5,858,515 A | 1/1999 | Stokes et al. | |
| 5,897,545 A | 4/1999 | Kline et al. | |
| 5,899,895 A | 5/1999 | Robles et al. | |
| 5,910,224 A | 6/1999 | Morman | |
| 5,997,521 A | 12/1999 | Robles et al. | |
| 6,030,373 A | 2/2000 | Van Gompel et al. | |
| 6,210,388 B1 | 4/2001 | Widlund et al. | |
| 6,213,991 B1 | 4/2001 | Kling et al. | |
| 6,287,287 B1 | 9/2001 | Elsberg | |
| 6,302,871 B1 | 10/2001 | Nakao et al. | |
| 6,413,249 B1 * | 7/2002 | Turi et al. | 604/387 |
| 6,461,344 B1 | 10/2002 | Widlund et al. | |
| 6,478,785 B1 * | 11/2002 | Ashton et al. | 604/385.01 |
| 2002/0052584 A1 | 5/2002 | Forgar | |
| 2003/0167049 A1 * | 9/2003 | Gibbs | 604/386 |

FOREIGN PATENT DOCUMENTS

| | | |
|---|---|---|
| GB | 1 520 740 | 8/1978 |
| WO | WO 95/27462 | 10/1995 |
| WO | WO 99/60969 | 12/1999 |
| WO | WO 00/35395 | 6/2000 |
| WO | WO 00/35398 | 6/2000 |
| WO | WO 00/37009 | 6/2000 |
| WO | WO 02/32365 A1 | 4/2002 |

* cited by examiner

ABSORBENT PANT GARMENTS HAVING OPTIMIZED LEG OPENING SHAPE

BACKGROUND OF THE INVENTION

This invention is directed to absorbent pant garments having fastening components on side panels in an orientation that minimizes the likelihood of fastener pop-opens.

Disposable absorbent pant garments, such as training pants, often include a pair of side panels with fastening systems that extend from a waist opening to a leg opening. The pant garments may be sold in a pre-fastened state such that the wearer can easily slip the pant on just as they would with regular underwear. The fastening system allows the wearer or a caregiver to remove and replace the pant without the need to remove outer pant garments or footwear.

While the fastening systems of disposable absorbent pant garments are beneficial in many respects, the nuisance of fastener "pop-opens" may result in less effective absorbent garments by allowing bodily wastes to spill out of a popped open side of the garment.

Fastening systems on diapers typically feature ears that attach to a landing zone on the tummy when applied to the wearer. Thus in diapers, leg stresses are spread over a larger portion of the garment compared to more pant-like garments, such as training pants. Since the stresses are more spread out, the stresses are less likely to concentrate at specific points. Furthermore, conventional diaper designs fit differently around the leg compared to conventional training pants. For example, diaper garments feature minimal coverage in the hip/leg area and are not as pant-like as conventional training pants. The absence of fasteners and stretchable materials in the upper leg area translates into leg bending stresses being much less of a concern for diapers than for training pants.

Training pants that feature stretchy sides that cover the entire hip and upper leg area of a wearer are under more point stress and tension than conventional diapers. In such training pants, stresses occur when the wearer bends his or her legs. Because the leg opening shape and fastener location can greatly impact the fastener security, or likelihood of pop-opens, the fasteners should be located on the garment in a location away from concentrated stress points.

There is a need or desire for absorbent pant garments having refastenable side seams with the fastening components located away from concentrated stress points in order to reduce the likelihood of fastener pop-opens.

SUMMARY OF THE INVENTION

In response to the discussed difficulties and problems encountered in the prior art, a new absorbent pant garment with refastenable side seams having strategically placed fastening components has been discovered. More specifically, the leg openings are designed such that the angle of the leg cut-out transfers the stresses away from the fastening components. Consequently, the fastening components, such as hook and loop fasteners, are less likely to disengage during product application and wear.

The absorbent pant garment includes an absorbent chassis that defines a waist opening and a pair of leg openings. Two pairs of front and back side panels are located on opposite transverse sides of the garment. A refastenable side seam, extending from the waist opening to one of the leg openings, is located between each pair of front and back side panels. A fastening component is bonded to an elastomeric layer of each of the front side panels adjacent a distal edge of each front side panel, and a mating fastening component is bonded to an elastomeric layer of each of the back side panels adjacent a distal edge of each back side panel. The fastening component and/or mating fastening component need not be fully bonded to a side panel, but instead may protrude from a side panel, suitably with a waist end edge of the fastener substantially parallel to a leg end edge of the fastener. Alternatively, the fastening component and/or mating fastening component may be integral with a side panel. The side panels themselves may be made of elastomeric material, such as stretch-bonded laminate, or may include an elastomeric core bonded to a side panel substrate. Furthermore, an entire layer of each side panel need not be elastomeric, as long as a portion of the side panel along a leg end edge is elastomeric. The elastomeric layer may be an elastic film or other elastomeric material, or may be elasticized by elastic strands.

Each of the front and back side panels includes a waist end edge and a leg end edge, with at least a portion of the waist end edge and a portion of the leg end edge substantially parallel to one another adjacent the distal edge for a distance greater than a transverse width of the fastening component bonded thereto. For example, the length of the substantially parallel portions of the waist end and leg end edges may be at least as long as a transverse width of a smaller fastening component of the refastenable seam, or at least 1.2 times the transverse width of the smaller fastening component of the refastenable seam, or at least 1.5 times the transverse width of the smaller fastening component of the refastenable seam, thereby avoiding any curved or angled edges directly above or directly below the fastening components, thus avoiding placement of the fastening components on any concentrated stress points. The leg end edges of any of the side panels may either be a straight continuation of the portion substantially parallel to the waist end edge, or may include another portion that is transversely offset from the fastening component and is non-parallel and non-perpendicular to the waist end edge. Similarly, the waist end edges of any of the side panels may either be a straight continuation of the portion substantially parallel to the leg end edge, or may include another portion that is transversely offset from the fastening component and is non-parallel and non-perpendicular to the leg end edge.

Each of the front and back side panels may either be separate panels permanently attached to an outer cover of the absorbent chassis along an attachment edge opposite the distal edge of each panel, or may be continuous extensions of the outer cover or any other layer of the chassis.

The fastening components on any or all of the side panels may be vertical such that the distal edges are substantially perpendicular to the portions of the waist end edges and leg end edges that are substantially parallel to one another. Alternatively, the fastening components on any or all of the side panels may be diagonal or other non-vertical position such that the distal edges are non-perpendicular to the portions of the waist end edges and leg end edges that are substantially parallel to one another.

Suitably, each of the side panels can be stretched by about 50% to about 400%, or about 100% to about 300%, or about 150% to about 250%, in a transverse direction, or in a direction substantially parallel to the parallel portions of the waist end and leg end edges.

With the foregoing in mind, it is a feature and advantage of the invention to provide an absorbent pant garment with refastenable side seams having a reduced likelihood of fastener pop-opens compared to conventional refastenable side seams.

BRIEF DESCRIPTION OF THE DRAWINGS

These and other objects and features of this invention will be better understood from the following detailed description taken in conjunction with the drawings, wherein.

DEFINITIONS

Within the context of this specification, each term or phrase below will include the following meaning or meanings.

"Absorbent pant garment" includes diaper pants, training pants, swim wear, absorbent underpants, adult incontinence products, feminine hygiene products, and the like. The term "disposable garment" includes garments that are typically disposed of after 1-5 uses.

"Elastomeric" and "elastic" refer to that property of a material or composite by virtue of which it tends to recover its original size and shape after removal of a force causing a deformation. It is generally preferred that the elastomeric material or composite be capable of being elongated by at least 50 percent, more preferably by at least 300 percent, of its relaxed length and recover, upon release of an applied force, at least 50 percent of its elongation.

"Layer" when used in the singular can have the dual meaning of a single element or a plurality of elements.

Figure 2:
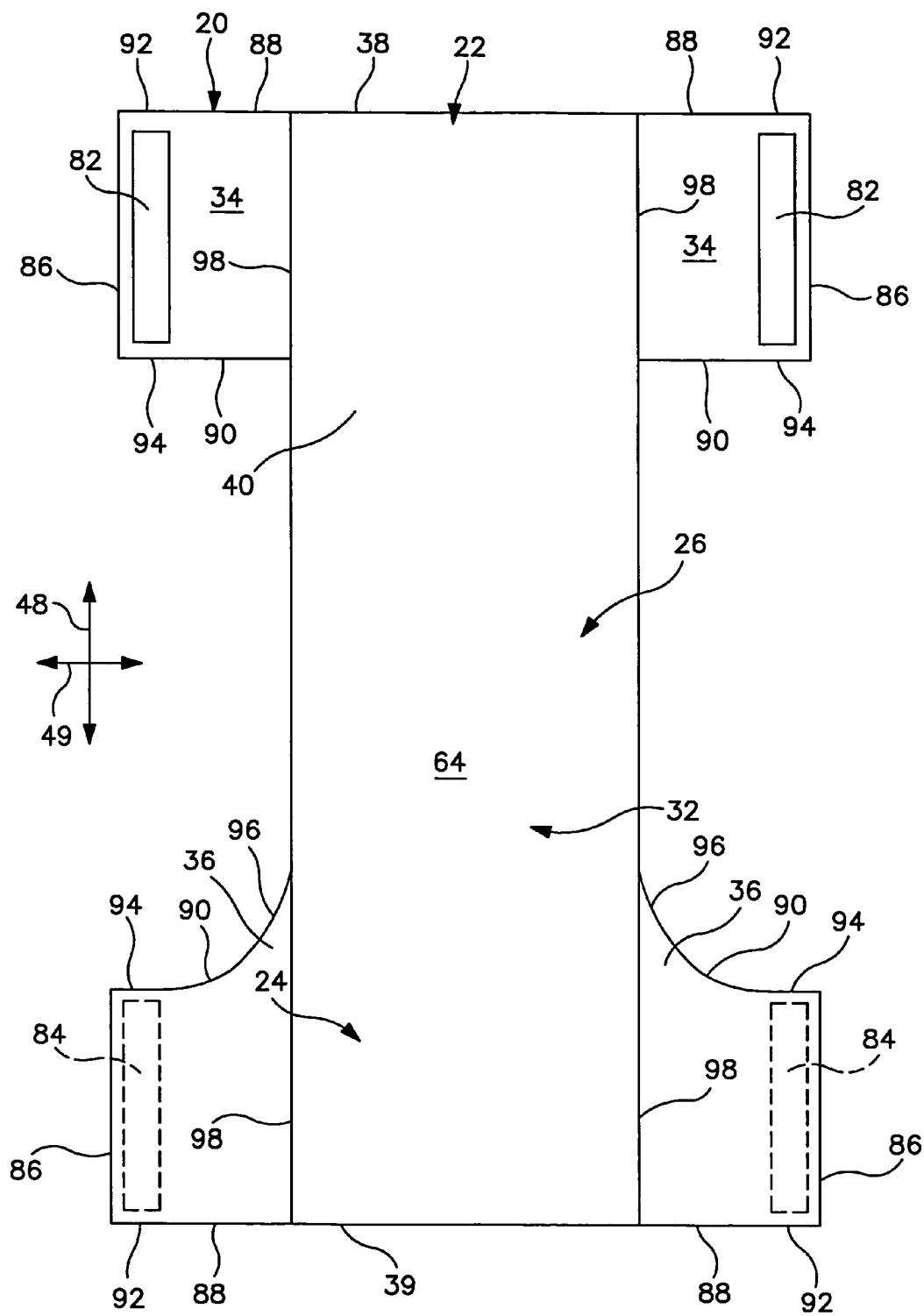
FIG. 2 is a plan view of another representative absorbent pant garment of the invention in a partially disassembled, stretched flat state, and showing the surface of the garment that faces away from the wearer when the article is worn.
Figure 3:
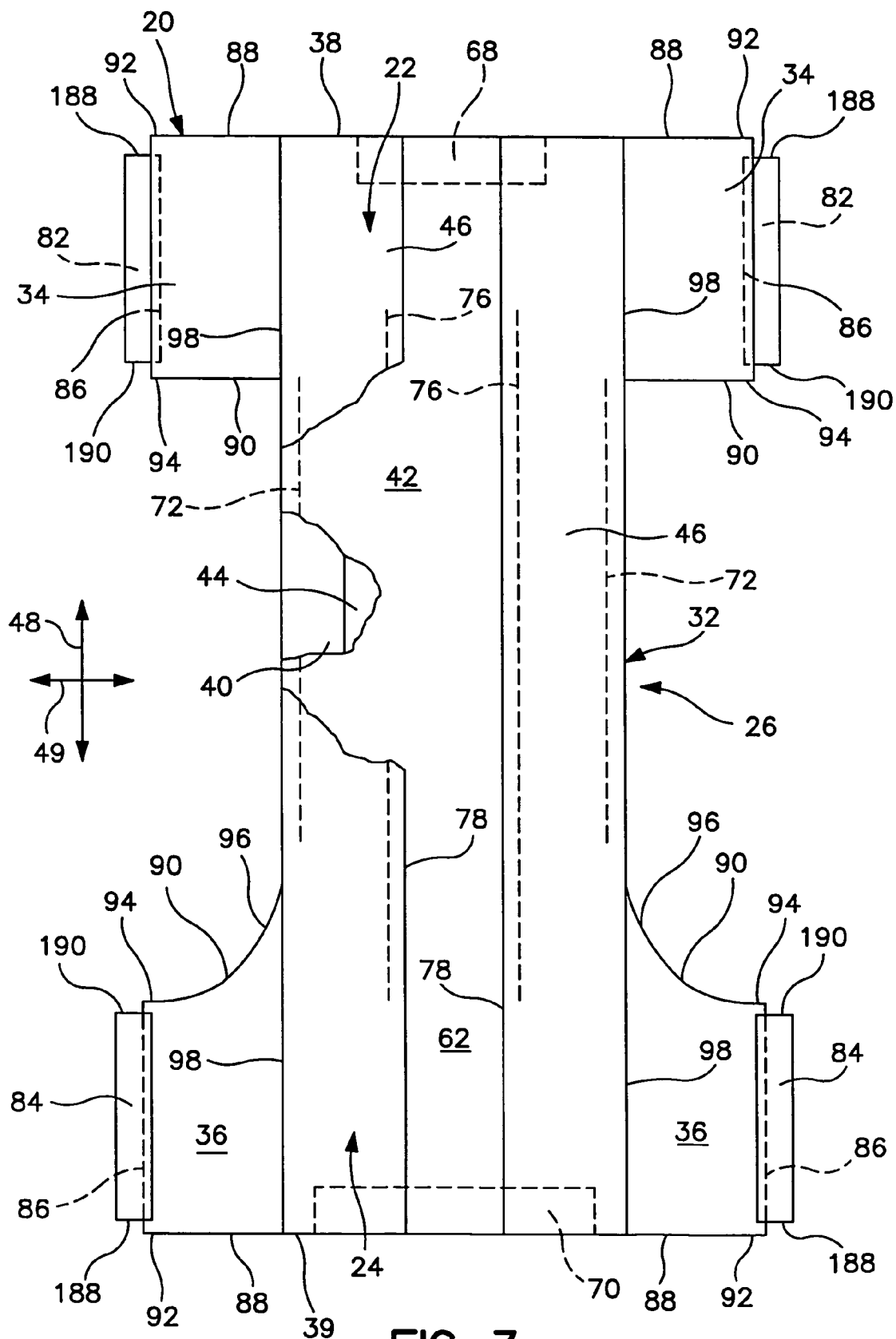
FIG. 3 is a plan view of the absorbent pant garment of FIG. 2 in a partially disassembled, stretched flat state, and showing the surface of the garment that faces the wearer when the article is worn, and with portions cut away to show underlying features.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Necked" refers to a method of elongating a nonwoven fabric, generally in the longitudinal, or machine direction, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. When relaxed, the web retracts toward its original dimensions.

"Nonwoven" or "nonwoven web" refers to materials and webs of material having a structure of individual fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Permanently attached" or "permanently bonded" refers to the joining, adhering, connecting, attaching, bonding, or the like, of two elements of an absorbent garment such that the elements tend to be and remain attached during normal use conditions of the absorbent garment.

"Refastenable," "releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Smaller fastening component" refers to either the fastening component or the mating fastening component of a single refastenable seam, having a smaller transverse width. In an embodiment in which one of the fastening components is integral with a layer of the garment chassis, the smaller fastening component is the non-integral fastening component.

"Stretch-bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Stretchable" refers to that property of a material or composite by virtue of which it can be stretched, without breaking, by at least 50% (to at least 150% of its initial (unstretched) length) in at least one direction, suitably by at least 100% (to at least 200% of its initial length), desirably by at least 150% (to at least 250% of its initial length). The term includes elastic materials as well as materials that stretch but do not significantly retract.

"Substantially parallel" refers to edges that are within 10 degrees of parallel to one another.

"Substantially perpendicular" refers to edges that are within 10 degrees of perpendicular to one another.

"Superabsorbent" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers.

DESCRIPTION OF PREFERRED EMBODIMENTS

The present invention is directed to absorbent pant garments having fastening components placed on side panels away from concentrated stress points. Consequently, the location of the fastening components and the shape of the fastening area about the leg opening minimize the likelihood of fastener pop-opens.

The principles of the present invention can be incorporated into any suitable disposable absorbent pant garment. Examples of such suitable garments include training pants, diaper pants, incontinence products, and other personal care or health care garments. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

Figure 1:
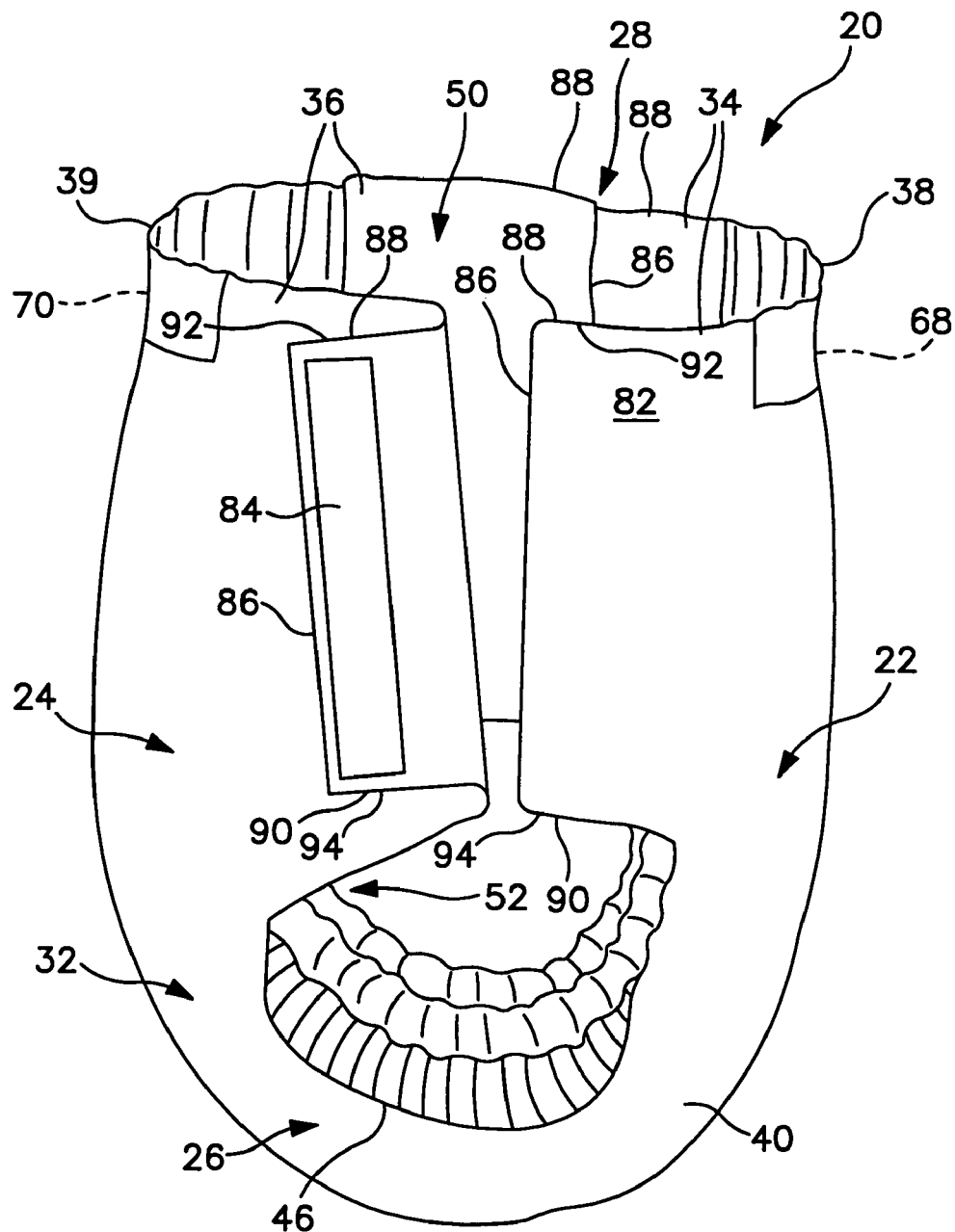
FIG. 1 is a side perspective view of a representative absorbent pant garment of the invention in a partially fastened state.

Referring to FIG. 1, a training pant 20 having refastenable side seams 28 is illustrated in a partially fastened condition. The training pant 20 includes an absorbent chassis 32 defining a three-dimensional pant configuration having a waist opening 50 and a pair of leg openings 52. The chassis 32 also includes a pair of transversely opposed front side panels 34 and a pair of transversely opposed back side panels 36, together forming refastenable side seams 28 connecting front and back regions of the garment. The front region 22 includes the portion of the training pant 20 which, when worn, is positioned on the front of the wearer while the back region 24 includes the portion of the training pant which, when worn, is positioned on the back of the wearer. A crotch region 26 of the training pant 20 includes the portion of the training pant which, when worn, is positioned between the legs of the wearer and covers the lower torso of the wearer. For reference, arrows 48 and 49 depicting the orientation of the longitudinal axis and the transverse axis, respectively, of the training pant 20 are illustrated in FIGS. 2 and 3.

The chassis 32 includes a body side liner 42 which is configured to contact the wearer, and an outer cover 40 opposite the body side liner which is configured to contact the wearer's clothing. An absorbent assembly 44 (FIG. 3) is positioned or located between the outer cover 40 and the body side liner 42. Each of these components is described in further detail below.

The refastenable side seams 28 are suitably lap seams, and may be formed using fastening components 82 that are adapted to refastenably connect to mating fastening components 84, with the fastening components 82 bonded to the front side panels 34 and the mating fastening components 84 bonded to the back side panels 36. The fastening components 82 and mating fastening components 84 may extend a full longitudinal length of the side panel 34, 36 to which each is bonded, or may extend only a partial longitudinal length of the respective side panel. The fastening components 82 and mating fastening components 84 may be rectangular, oval, or any other suitable shape, including irregular shapes. Furthermore, the fastening components 82 and/or mating fastening components 84 need not be fully bonded to a side panel 34, 36, but instead may protrude from a side panel, with a waist end edge of the fastener substantially parallel to a leg end edge of the fastener. As another alternative, the fastening components 82 and/or the mating fastening components 84 may be integral with the outer cover or body side liner, such that the material used to form the outer cover or body side liner may serve as a fastening component or mating fastening component. FIG. 1, for example, illustrates an outer cover 40 with the fastening components 82 integral with the outer cover. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners.

Loop type fasteners typically include a fabric or nonwoven material having a plurality of loop members extending outwardly from at least one surface of the backing structure. The loop material can be formed of any suitable material, such as acrylic, nylon, polyester, polypropylene, or polyethylene, and can be formed by methods such as spunbonding, meltblowing, warp knitting, stitch bonding, needle punching, nonwoven laminates, bonded carded webs, point-unbonded material, and other methods known in the art. Point-unbonded materials, for example, are taught in U.S. Pat. No. 5,858,515 issued to Stokes, et al., herein incorporated by reference. Suitable loop materials are available from Guilford Mills, Inc., Greensboro, N.C., U.S.A. In one embodiment, the outer cover material and/or the body side liner material may serve as a loop type fastener.

Hook type fasteners typically include a fabric or material having a base or backing structure and a plurality of hook members extending upwardly from at least one surface of the backing structure. Suitable single-sided hook materials for the fastening components 82 or the mating fastening components 84 are available from Velcro Industries B.V., Amsterdam, Netherlands or affiliates thereof. In one embodiment, the outer cover material and/or the body side liner material may serve as a hook type fastener.

The front side panel 34 may overlap the back side panel 36, or vice-versa, with the fastening component 82 attached to an inner surface 62 of the front side panel 34 and the mating fastening component 84 attached to an outer surface 64 of the back side panel 36, or vice-versa. The fastening component 82 on each front side panel 34 is bonded to the front side panel adjacent a distal edge 86 of the front side panel, as shown in FIGS. 2 and 3. Similarly, the mating fastening component 84 on each back side panel 36 is bonded to the back side panel adjacent a distal edge 86 of the back side panel, as shown in FIGS. 2 and 3. In one embodiment, as shown in FIG. 3, the fastening components 82 and/or mating fastening components 84 can be bonded to the respective side panel adjacent a distal edge 86 and may extend beyond the distal edge 86.

Each of the front side panels 34 includes a waist end edge 88 and a leg end edge 90, with a portion 92 of the waist end edge and a portion 94 of the leg end edge substantially parallel to one another adjacent the distal edge 86. The parallel portions 92, 94 of the waist end edge 88 and the leg end edge 90 of the front side panels run substantially parallel to one another for a distance greater than a transverse width of the smaller fastening component 82 or 84 of the refastenable seam formed with a back side panel 36, the smaller fastening component being bonded between the two parallel portions 92, 94. Likewise, each of the back side panels 36 includes a waist end edge 88 and a leg end edge 90 with a portion 92 of the waist end edge and a portion 94 of the leg end edge substantially parallel to one another adjacent the distal edge 86. As in the front side panels 34, the parallel portions 92, 94 of the waist end edge 88 and the leg end edge 90 of the back side panels 36 suitably run substantially parallel to one another for a distance greater than a transverse width of the smaller fastening component 82 or 84 of the refastenable seam formed with a front side panel 34, the smaller fastening component being bonded between the two parallel portions. Alternatively, in an embodiment in which the fastening components 82 and/or mating fastening components 84 extend from the side panels (FIG. 3), the parallel portions 92, 94 of the side panels are substantially parallel to one another for a distance of at least a transverse width of any overlap between the side panel and the fastening component bonded thereto, and a waist end edge 188 and a leg end edge 190 of the fastening components 82, 84 are substantially parallel to one another as well as substantially parallel to the parallel portions 92, 94 of the side panels, as shown in FIG. 3. As another alternative, in an embodiment in which the fastening components 82 or the mating fastening components 84 are integral with the outer cover 40 or body side liner 42, the parallel portions 92, 94 of the side panels with the integral fastener extend transversely for a distance of at least the transverse width of the non-integral fastening components 82 or mating fastening components 84 on the corresponding side panel of the same refastenable seam.

Figure 7:
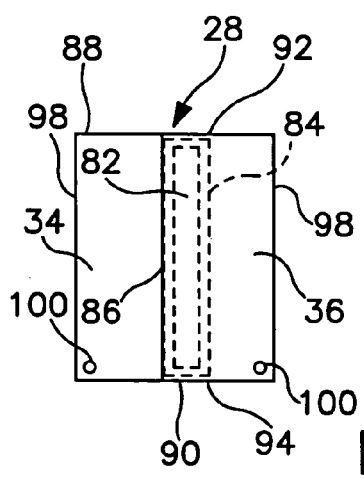
Figure 8:
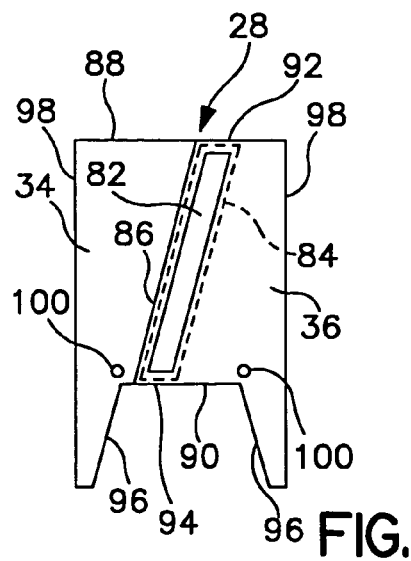

The fastening components 82 and mating fastening components 84 may be attached to the side panels 34, 36 either vertically, or diagonally, or in a non-linear fashion. For example, when the fastening components 82, 84 are attached to the side panels 34, 36 vertically, the distal edges 86 of the side panels to which the fastening components are attached are suitably substantially perpendicular to the parallel portions 92, 94 of the waist end edges 88 and the leg end edges 90, as shown in the illustrated side panels 34, 36 in FIGS. 4-7 and 9. As another example, when the fastening components 82, 84 are attached to the side panels 34, 36 non-vertically, the distal edges 86 of the side panels to which the fastening components are attached are suitably non-perpendicular to the parallel portions 92, 94 of the waist end edges 88 and the leg end edges 90, as shown in FIG. 8.

Because the leg opening shape and the fastener location can greatly impact the fastener security (pop-opens), side panel stresses should not be directly applied to the fastening components 82, 84. It has been found that stress points in side panels of pant garments are concentrated at corners where angled portions 96 meet the parallel edge portions 92 or 94. These concentrated stress points 100 are determined qualitatively, namely by observing where the product starts to pull away or degrade. The areas of concentrated stress points 100 are indicated in the illustrated side panels 34, 36 in FIGS. 4-9, keeping in mind that additional stress points may be present in less concentrated areas around the leg openings. The parallel portions 92, 94 of the waist end edges 88 and leg end edges 90 are provided to distance the fastening components 82 and the mating fastening components 84 away from concentrated stress points 100. More particularly, the side panels 34, 36 are designed such that there is no curvature along the leg end edges 90 longitudinally aligned with the fastening components 82, 84, with any curvature along the leg end edges being transversely offset from the fastening components. If the leg openings 52 are designed such that the angle of the leg cut transfers the stresses directly away from the fastener, then the fastening components 82, 84 are less likely to disengage during product application and wear. Therefore, the parallel portions 92, 94 of the waist end edges 88 and leg end edges 90 suitably have a length greater than the transverse width of the smaller fastening component of the refastenable seam formed therebetween, or a length of at least 1.2 times the transverse width of the smaller fastening component of the refastenable seam formed therebetween (FIG. 4), or a length of at least 1.5 times the transverse width of the smaller fastening component of the refastenable seam formed therebetween (FIG. 5), to provide sufficient spacing between the fastening components 82, 84 and the concentrated stress points 100.

Figure 4:
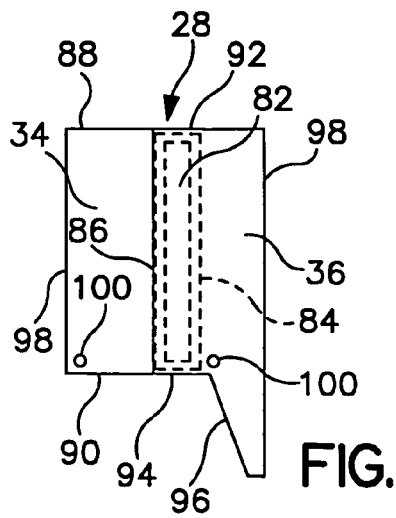
FIGS. 4-9 illustrate releasably engaged side panels in a fastened state.
Figure 5:
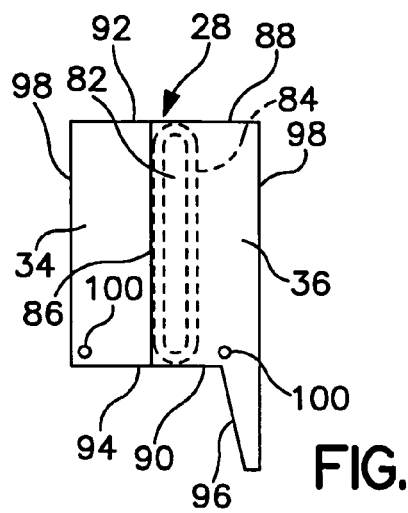
Figure 6:
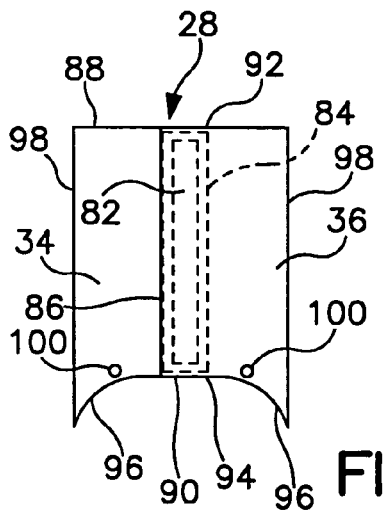
Figure 9:
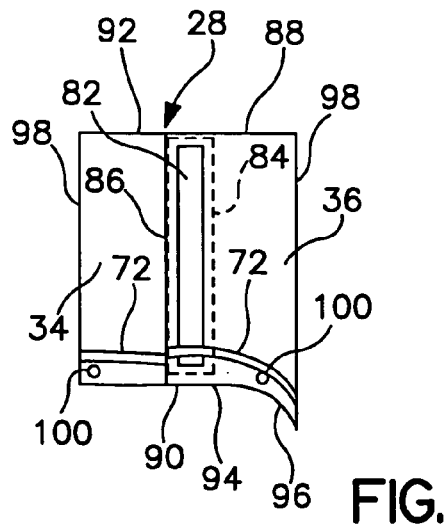

In addition to the parallel portions 94 of the leg end edges, the leg end edges 90 may also include a portion 96 transversely offset from the fastening components 82 or mating fastening components 84 that is non-parallel and non-perpendicular to the waist end edge 88. As shown in FIGS. 4 and 5, just the leg end edges 90 of the back side panels 36 may include these angled portions 96 while the leg end edges 90 of the front side panels 34 may be straight along the entire length of the leg end edges. Alternatively, as shown in FIGS. 6 and 8, the leg end edges 90 of both the front side panels 34 and the back side panels 36 may include angled portions 96. The transition between the parallel portions 92, 94 and the angled portions 96 may either be in the form of sharp corners (FIGS. 4, 5, 8) or curvilinear corners (FIGS. 6 and 9). In another embodiment of the invention, the entire length of the leg end edges 90 of both the front side panels 34 and the back side panels 36 may be straight lines substantially parallel to the parallel portions 92 of the waist end edges 88, as shown in FIG. 7.

The side panels 34, 36 may either be separate panels permanently attached to the front and back regions 22, 24 of the absorbent chassis 32 along attachment edges 98 of the side panels 34, 36, as shown in FIGS. 2 and 3, using attachment means known to those skilled in the art such as adhesive, thermal or ultrasonic bonding, or alternatively, may be continuous extensions of the outer cover 40 and/or body side liner 42 of the absorbent chassis, as shown in FIG. 1. The side panels 34, 36, whether separately attached to the front and back regions or integral with the front and back regions, extend from the waist opening 50 to one of the leg openings 52.

Each of the side panels 34, 36 can include one or more individual, distinct pieces of material. The side panels 34, 36 suitably include an elastic material capable of stretching in a direction substantially parallel to the transverse axis 49 of the training pant 20, or in a direction substantially parallel to the parallel portions 92, 94 of the leg end and waist end edges of the side panels, which are suitably also substantially parallel to the transverse axis 49. Alternatively, the side panels may include an elastic material capable of stretching in a direction substantially non-parallel to the parallel portions 92, 94 of the leg end and waist end edges of the side panels. As yet another alternative, the side panels may include an elastic material capable of stretching in multiple directions.

Suitable elastic materials, as well as processes of incorporating side panels into a training pant, are known to those skilled in the art, and are described, for example, in U.S. Pat. No. 4,940,464 issued Jul. 10, 1990 to Van Gompel et al., which is incorporated herein by reference. Suitably, the side panels 34, 36 can be stretched by about 50% to about 400%, or by about 100% to about 300%, or by about 150% to about 250%. The side panels 34, 36 may be entirely elastomeric, made up of a stretch-bonded laminate of KRATON elastomeric materials, available from Kraton Polymers of Belpre, Ohio, laminated between two layers of spunbonded webs, for example, or may include an elastomeric core, made up of KRATON or LYCRA spandex, for example, bonded to a non-elastomeric substrate such as a spunbonded or meltblown web. When an elastic carrier sheet is used, the leg opening shape is still important, but less critical than when an entire elastic side panel is used. The attachment (i.e., ultrasonic bonding) of the carrier sheet to the side panel usually creates a no-stretch zone equal to the width of the bond pattern. For a garment with a shaped leg opening, the no-stretch zone alone can not "absorb" forces from transferring to the fastening components. If the no-stretch zone does absorb the forces, then the no-stretch zone deadens too much area and compromises stretch. Therefore, the location of the fastening components 82, 84 between parallel portions 92, 94 of the leg end and waist end edges of the side panels, as described herein, is an important feature of the elastomeric side panels 34, 36. In yet another embodiment, the side panels 34, 36 may include a non-elastomeric substrate such as a spunbonded or meltblown web, with one or more elastic strands, such as leg elastics 72 (described below), along the leg end edge 90 of the side panels 34, 36, as shown in FIG. 9. Furthermore, the front side panels 34 may differ from the back side panels 36 in terms of construction. In any case, at least a portion of at least one of the layers to which the fastening components 82, 84 are bonded are elastomeric. Some of the underlying stretch of the elastomeric layer is deadened upon bonding the fastening components thereto. Thus, when the fastening components 82 and mating fastening components 84 are engaged, even with stretchable fasteners, stretchability of the region on which the fastening components 82, 84 are located is reduced. The most critical stretch is in the side panel areas where the fastening components are not located, hence the need for the location of the fastening components between the parallel portions 92, 94 of the leg end and waist end edges of the side panels distanced from the concentrated stress points 100.

The outer cover 40 suitably covers the front region 22, crotch region 26, and back region 24. As mentioned, in certain embodiments the outer cover 40 may also cover, or form, the side panels 34, 36 as well, creating an all-encompassing, one-piece garment exterior. The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable body side liner 42 is made. While it is not a necessity for the outer layer to be liquid permeable, it is desired that it provides a relatively cloth-like texture to the wearer.

Necked-bonded laminates and neck-stretched elastic laminates are particularly suitable for forming the outer cover 40. Necked-bonded laminates, in general, include at least one layer of necked or neckable material bonded to a stretchable or elastomeric layer. Necked-bonded laminates, and methods of making necked-bonded laminates, are taught, for example, in U.S. Pat. No. 5,910,224 to Morman, incorporated herein by reference. Neck-stretched elastic laminate material can be made by (1) elongating a nonwoven facing in a machine direction which allows it to neck down in the cross direction (i.e., "neck stretching"), (2) laminating the resulting necked facing to an elastic substrate while it is elongated in the machine direction, and (3) post bonding the resultant laminate in a relaxed or semi-relaxed state. The necking of the facing provides the ability for the material to be extended in the cross direction to about its pre-necked width. The stretch-bonding laminating process takes the necked facings and attaches them to a stretched elastic material. The stretched elastic material then gathers the nonwoven facing in the machine direction when the stretching force is released. Post bonding the relaxed or semi-relaxed laminate as a subsequent third step may or may not interfere with the extension and retraction of the laminate, depending on the bond pattern and area covered. Other types of material suitable for the outer cover 40 include stretch-thermal laminates, reversibly necked laminates, and stretch-bonded laminates. Methods of making such elastic materials are well known to those skilled in the art and are described in U.S. Pat. No. 4,663,220 issued to Wisneski et al.; U.S. Pat. No. 5,226,992 issued to Morman; and European Patent Application No. EP 0 217 032 published on Apr. 8, 1987 in the names of Taylor et al; all of which are incorporated herein by reference. Any of these materials may also be suitable for use in forming the side panels or practically any other components of the garment.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Pliant Corporation of Schaumburg, Ill., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable breathable material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Certain non-breathable elastic films can also be used to make the outer cover 40. Examples of suitable non-breathable films can be made of styrene-ethylene-butylene-styrene or styrene-isoprene-styrene block copolymers, KRATON polymers from Kraton Polymers USLLC of Belpre, Ohio, U.S.A., metallocene catalyzed elastomers or plastomers, and the like. Other materials suitable for making the outer cover 40 include monolithic breathable films, such as those made of polyether amide based polymers, for example PEBAX, and ether/ester polyurethane thermal-plastic elastomers.

The liquid permeable body side liner 42 is illustrated as overlying the outer cover 40 and absorbent assembly 44, and may but need not have the same dimensions as the outer cover 40. The body side liner 42 is desirably compliant, soft feeling, and non-irritating to the wearer's skin. Further, the body side liner 42 can be less hydrophilic than the absorbent assembly 44, to present a relatively dry surface to the wearer and permit liquid to readily penetrate through its thickness.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL™ N-62 available from available from Uniqema Inc., a division of ICI of New Castle, Del., U.S.A. and GLUCOPON™ 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and body side liner 42 can include elastomeric materials, it can be desirable in some embodiments for the composite structure to be generally inelastic, where the outer cover, the body side liner and the absorbent assembly include materials that are generally not elastomeric.

The absorbent assembly 44 can be any structure which is generally compressible, conformable, non-irritating to the wearer's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The absorbent assembly 44 can have variable thickness, with greater thickness in target areas, such as in a central portion of the crotch region. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 can include an extremely thin absorbent composite material sold under the trade name NOVATHIN™ available from Rayonier Corporation located in Jessup, Ga., U.S.A., and/or an ultra-thin-absorbent (UTA) material including a mixture of SAP and pulp fiber. An example of a suitable UTA may include 3.7 grams (g) of FAVOR™ SXM 9543 SAP, available from Stockhausen GmbH & Co. KG located in Krefeld, Fed. Rep. of Germany, and 3.7 g of NB416 pulp fiber available from Weyerhauser located in Federal Way.

The chassis 32 can also incorporate other materials that are designed primarily to receive, temporarily store, and/or transport liquid along the mutually facing surface with the absorbent assembly 44, thereby maximizing the overall absorbent capacity of the absorbent assembly 44, if desired. One suitable material is referred to as a surge layer.

To further enhance containment and/or absorption of body exudates, the training pant 20 may include a front waist elastic member 68, a rear waist elastic member 70, and leg elastic members 72, as are known to those skilled in the art (FIG. 3). The waist elastic members 68, 70 can be operatively joined to the outer cover 40 and/or body side liner 42 along opposite waist edges 38 and 39, and can extend over part or all of the waist edges. The leg elastic members 72 are desirably operatively joined to the outer cover 40 and/or body side liner 42 along opposite side edges of the chassis 32 and positioned in the crotch region 26 of the training pant 20.

The waist elastic members 68, 70 and the leg elastic members 72 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 72 include a plurality of dry-spun coalesced multifilament spandex elastomeric threads sold under the trade name LYCRA™ and available from E. I. DuPont de Nemours and Company, Wilmington, Del., U.S.A.

To enhance containment and/or absorption of any body exudates discharged from the wearer, the chassis 32 may include a pair of containment flaps 46 which are configured to provide a barrier to the transverse flow of body exudates. A flap elastic member 76 (FIG. 3) may be operatively joined with each containment flap 46 in any suitable manner as is well known in the art. The elasticized containment flaps 46 define an unattached edge 78 which assumes an upright, generally perpendicular configuration in at least the crotch region 26 of the training pant 20 to form a seal against the wearer's body. The containment flaps 46 can be located along the leg openings, encircling at least a portion of each of the leg openings. Suitable constructions and arrangements for the containment flaps 46 are generally well known to those skilled in the art.

The side panel design and fastening component placement of this invention eliminate a need for releasable side bonds (passive bonds) by providing a shaped leg opening with the concentrated stresses away from the fastening components. Thus, this invention makes it possible to provide a secure fastening system in a pre-fastened and refastenable pull-on garment 20.

As described herein, the various components of the absorbent garment can be assembled together employing various types of suitable attachment means, such as adhesive, sonic and thermal bonds or combinations thereof. The resulting product is an absorbent pant garment having desirable side panel shapes and fastening component locations for minimizing fastener pop-opens.

EXAMPLE

Refastenable Seam 1

Figure 10:
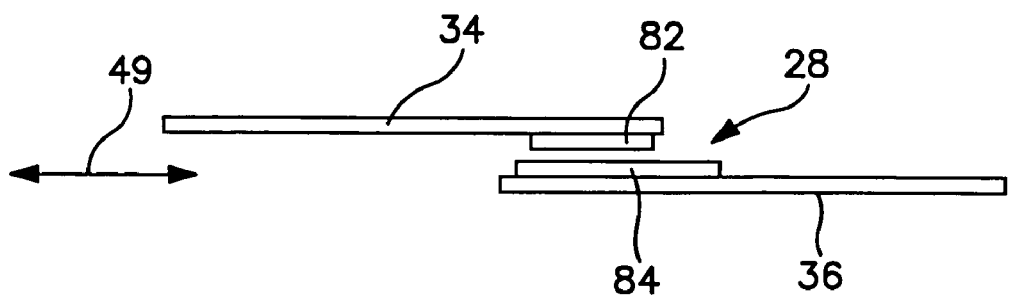
FIGS. 10 and 11 illustrate representative end views of refastenable seams of absorbent pant garments of the invention.

As shown in FIG. 10, a hook component 82 on a front side panel 34 can form a refastenable seam 28 with a loop component 84 on a back side panel 36. If the hook component has a transverse width of 16 millimeters (mm), and the loop component has a transverse width of 25 mm, the parallel portions of the waist end edge and leg end edge of the front and back side panels (shown in FIGS. 2-9) are at least 16 mm long in the transverse direction, in accordance with the invention. Furthermore, if the parallel portions must be at least 1.2 times the width of the smaller fastening component, which in this case is the hook component, the parallel portions must be at least 19 mm long in the transverse direction. Furthermore, if the parallel portions must be at least 1.5 times the width of the smaller fastening component, the parallel portions must be at least 24 mm long in the transverse direction.

Refastenable Seam 2

Figure 11:
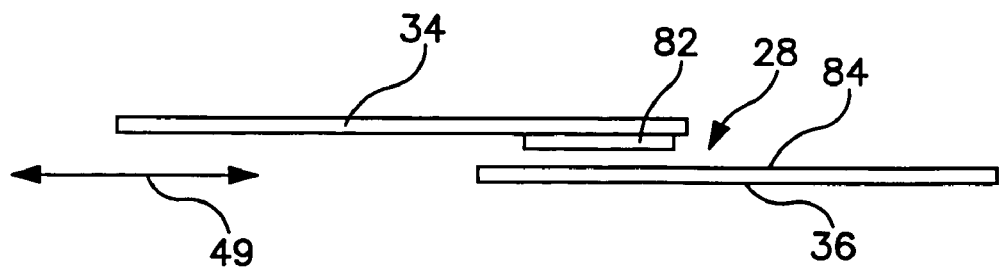

As shown in FIG. 11, the back side panel 36 may be made up of a material that serves as loop material 84 in conjunction with the hook fastener 82 on the front side panel 34. In this case, the hook component is considered the smaller fastening component since the loop component is relatively undefined in shape. Therefore, if the hook component has a transverse width of 16 mm, all of the same parallel portion length requirements for refastenable seam 1 (FIG. 10) apply to refastenable seam 2 (FIG. 11).

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An absorbent pant garment, comprising:
an absorbent chassis defining a waist opening and first and second leg openings;
a first front side panel and a first back side panel forming a first refastenable seam there between, wherein the first refastenable seam is refastenable from the waist opening to the first leg opening, with a first fastening component on a first surface of an elastomeric layer of the first front side panel adjacent to a distal edge of the first front side panel refastenably connected to a first mating fastening component on a second surface of the first back side panel adjacent to a distal edge of the first back side panel, wherein the second surface is opposite the first surface, one of the first fastening component and the first mating fastening component being a smaller fastening component of the first refastenable seam;
a second front side panel and a second back side panel forming a second refastenable seam there between, wherein the second refastenable seam is refastenable from the waist opening to the second leg opening, with a second fastening component on a first surface of an elastomeric layer of the second front side panel adjacent to a distal edge of the second front side panel refastenably connected to a second mating fastening component on a second surface of the second back side panel adjacent to a distal edge of the second back side panel, wherein the second surface is opposite the first surface, one of the second fastening component and the second mating fastening component being a smaller fastening component of the second refastenable seam;
wherein each of the first and second front side panels includes a waist end edge, a distal edge, and a leg end edge, with a portion of the waist end edge and a portion of the leg end edge substantially parallel to one another adjacent the distal edge for a distance greater than a transverse width of the smaller fastening component of the corresponding refastenable seam;
wherein each of the first and second back side panels includes a waist end edge, a distal edge, and a leg end edge, with a portion of the waist end edge and a portion of the leg end edge substantially parallel to one another adjacent the distal edge for a distance greater than a transverse width of the smaller fastening component of the corresponding refastenable seam; and
wherein the absorbent chassis has an outer cover that forms the first and second front and back side panels to create a one-piece garment exterior.

2. The absorbent pant garment of claim 1, wherein the portion of the waist end edge and the portion of the leg end edge of each of the first and second back side panels are substantially parallel to one another adjacent the distal edge for a distance of at least 1.2 times the transverse width of the smaller fastening component of the corresponding refastenable seam.

3. The absorbent pant garment of claim 1, wherein the portion of the waist end edge and the portion of the leg end edge of each of the first and second back side panels are substantially parallel to one another adjacent the distal edge for a distance of at least 1.5 times the transverse width of the smaller fastening component of the corresponding refastenable seam.

4. The absorbent pant garment of claim 1, wherein the portion of the waist end edge and the portion of the leg end edge of each of the first and second front side panels are substantially parallel to one another adjacent the distal edge for a distance of at least 1.2 times the transverse width of the smaller fastening component of the corresponding refastenable seam.

5. The absorbent pant garment of claim 1, wherein the portion of the waist end edge and the portion of the leg end edge of each of the first and second front side panels are substantially parallel to one another adjacent the distal edge for a distance of at least 1.5 times the transverse width of the smaller fastening component of the corresponding refastenable seam.

6. The absorbent pant garment of claim 1, wherein the first fastening component is integral with the first front side panel and the second fastening component is integral with the second front side panel.

7. The absorbent pant garment of claim 1, wherein the first mating fastening component is integral with the first back side panel and the second mating fastening component is integral with the second back side panel.

8. The absorbent pant garment of claim 1, wherein the first fastening component is bonded to the first front side panel and the second fastening component is bonded to the second front side panel.

9. The absorbent pant garment of claim 1, wherein the first mating fastening component is bonded to the first back side panel and the second mating fastening component is bonded to the second back side panel.

10. The absorbent pant garment of claim 1, wherein the first fastening component is bonded to and extends past the distal edge of the first front side panel and the second fastening component is bonded to and extends past the distal edge of the second front side panel.

11. The absorbent pant garment of claim 1, wherein the first mating fastening component is bonded to and extends past the distal edge of the first back side panel and the second mating fastening component is bonded to and extends past the distal edge of the second back side panel.

12. The absorbent pant garment of claim 1, wherein the first mating fastening component is bonded to and extends past the distal edge of the first back side panel and the second mating fastening component is bonded to and extends past the distal edge of the second back side panel.

13. The absorbent pant garment of claim 1, wherein the leg end edge of each of the first and second back side panels further comprises a portion transversely offset from the first and second mating fastening components that is non-parallel and non-perpendicular to the waist end edge of each of the first and second back side panels.

14. The absorbent pant garment of claim 1, wherein the leg end edge of each of the first and second front side panels further comprises a portion transversely offset from the first and second fastening components that is non-parallel and non-perpendicular to the waist end edge of each of the first and second front side panels.

15. The absorbent pant garment of claim 1, wherein each of the side panels is permanently attached to the outer cover of the absorbent chassis along an attachment edge opposite the distal edge of each side panel.

16. The absorbent pant garment of claim 1, wherein each of the side panels is continuous with a layer of the absorbent chassis.

17. The absorbent pant garment of claim 1, wherein the distal edge of each of the first and second back side panels is perpendicular to the portion of the waist end edge and the portion of the leg end edge that are substantially parallel to one another.

18. The absorbent pant garment of claim 1, wherein the distal edge of each of the first and second back side panels is non-perpendicular to the portion of the waist end edge and the portion of the leg end edge that are substantially parallel to one another.

19. The absorbent pant garment of claim 1, wherein the distal edge of each of the first and second front side panels is perpendicular to the portion of the waist end edge and the portion of the leg end edge that are substantially parallel to one another.

20. The absorbent pant garment of claim 1, wherein the distal edge of each of the first and second side panels is non-perpendicular to the portion of the waist end edge and the portion of the leg end edge that are substantially parallel to one another.

21. The absorbent pant garment of claim 1, wherein the elastomeric layer of each of the front side panels comprises an elastic core.

22. The absorbent pant garment of claim 1, wherein the elastomeric layer of each of the front side panels comprises a stretch-bonded laminate.

23. The absorbent pant garment of claim 1, wherein each of the front side panels is stretchable in a direction substantially parallel to the substantially parallel portions of the waist end and leg end edges.

24. The absorbent pant garment of claim 1, wherein each of the front side panels is stretchable in a direction substantially non-parallel to the substantially parallel portions of the waist end and leg end edges.

25. The absorbent pant garment of claim 1, wherein each of the front side panels is stretchable in multiple directions.

26. The absorbent pant garment of claim 1, wherein the outer cover forms part of a laminate that comprises the front and back side panels.

27. An absorbent pant garment, comprising:
an absorbent chassis defining a waist opening and first and second leg openings;
a first front side panel and a first back side panel forming a first refastenable seam there between, wherein the first refastenable seam is refastenable from the waist opening to the first leg opening, with a first fastening component on a first surface of the first front side panel adjacent to a distal edge of the first front side panel refastenably connected to a first mating fastening component on a second surface of an elastomeric layer of the first back side panel adjacent to a distal edge of the first front side panel refastenably connected to a first mating fastening component on a second surface of an elastomeric layer of the first back side panel adjacent to a distal edge of the first back side panel, wherein the second surface is opposite the first surface, one of the first fastening component and the first mating fastening component being a smaller fastening component of the first refastenable seam;
a second front side panel and a second back side panel forming a second refastenable seam there between, wherein the second refastenable seam is refastenable from the waist opening to the second leg opening, with a second fastening component on a first surface of the second front side panel adjacent to a distal edge of the second front side panel refastenably connected to a second mating fastening component on a second surface of an elastomeric layer of the second back side panel adjacent to a distal edge of the second back side panel, wherein the second surface is opposite the first surface, one of the second fastening component and the second mating fastening component being a smaller fastening component of the second refastenable seam;
wherein each of the first and second front side panels includes a waist end edge, a distal edge, and a leg end edge, with a portion of the waist end edge and a portion of the leg end edge substantially parallel to one another adjacent the distal edge for a distance greater than a transverse width of the smaller fastening component of the corresponding refastenable seam; and
wherein each of the first and second back side panels includes a waist end edge, a distal edge, and a leg end edge, with a portion of the waist end edge and a portion of the leg end edge substantially parallel to one another adjacent the distal edge for a distance greater than a transverse width of the smaller fastening component of the corresponding refastenable seam; and
wherein the absorbent chassis has an outer cover that forms the first and second front and back side panels to create a one-piece garment exterior.

28. The absorbent pant garment of claim 27, wherein the portion of the waist end edge and the portion of the leg end edge of each of the first and second back side panels are substantially parallel to one another adjacent the distal edge for a distance of at least 1.2 times the transverse width of the smaller fastening component of the corresponding refastenable seam.

29. The absorbent pant garment of claim 27, wherein the portion of the waist end edge and the portion of the leg end edge of each of the first and second back side panels are substantially parallel to one another adjacent the distal edge for a distance of at least 1.5 times the transverse width of the smaller fastening component of the corresponding refastenable seam.

30. The absorbent pant garment of claim 27, wherein the portion of the waist end edge and the portion of the leg end edge of each of the first and second front side panels are substantially parallel to one another adjacent the distal edge for a distance of at least 1.2 times the transverse width of the smaller fastening component of the corresponding refastenable seam.

31. The absorbent pant garment of claim 27, wherein the portion of the waist end edge and the portion of the leg end edge of each of the first and second front side panels are substantially parallel to one another adjacent the distal edge for a distance of at least 1.5 times the transverse width of the smaller fastening component of the corresponding refastenable seam.

32. The absorbent pant garment of claim 27, wherein the first fastening component is integral with the first front side panel and the second fastening component is integral with the second front side panel.

33. The absorbent pant garment of claim 27, wherein the first mating fastening component is integral with the first back side panel and the second mating fastening component is integral with the second back side panel.

34. The absorbent pant garment of claim 27, wherein the first fastening component is bonded to the first front side panel and the second fastening component is bonded to the second front side panel.

35. The absorbent pant garment of claim 27, wherein the first mating fastening component is bonded to the first back side panel and the second mating fastening component is bonded to the second back side panel.

36. The absorbent pant garment of claim 27, wherein the first fastening component is bonded to and extends past the distal edge of the first front side panel and the second fastening component is bonded to and extends past the distal edge of the second front side panel.

37. The absorbent pant garment of claim 27, wherein the first mating fastening component is bonded to and extends past the distal edge of the first back side panel and the second mating fastening component is bonded to and extends past the distal edge of the second back side panel.

38. The absorbent pant garment of claim 27, wherein the leg end edge of each of the first and second back side panels further comprises a portion transversely offset from the first and second mating fastening components that is non-parallel and non-perpendicular to the waist end edge of each of the first and second back side panels.

39. The absorbent pant garment of claim 27, wherein the leg end edge of each of the first and second front side panels further comprises a portion transversely offset from the first and second fastening components that is non-parallel and non-perpendicular to the waist end edge of each of the first and second front side panels.

40. The absorbent pant garment of claim 27, wherein each of the side panels is permanently attached to the outer cover of the absorbent chassis along an attachment edge opposite the distal edge of each side panel.

41. The absorbent pant garment of claim 27, wherein each of the side panels is continuous with a layer of the absorbent chassis.

42. The absorbent pant garment of claim 27, wherein the distal edge of each of the first and second back side panels is perpendicular to the portion of the waist end edge and the portion of the leg end edge that are substantially parallel to one another.

43. The absorbent pant garment of claim 27, wherein the distal edge of each of the first and second back side panels is non-perpendicular to the portion of the waist end edge and the portion of the leg end edge that are substantially parallel to one another.

44. The absorbent pant garment of claim 27, wherein the distal edge of each of the first and second front side panels is perpendicular to the portion of the waist end edge and the portion of the leg end edge that are substantially parallel to one another.

45. The absorbent pant garment of claim 27, wherein the distal edge of each of the first and second front side panels is non-perpendicular to the portion of the waist end edge and the portion of the leg end edge that are substantially parallel to one another.

46. The absorbent pant garment of claim 27, wherein the elastomeric layer of each of the back side panels comprises an elastic core.

47. The absorbent pant garment of claim 27, wherein the elastomeric layer of each of the back side panels comprises a stretch-bonded laminate.

48. The absorbent pant garment of claim 27, wherein each of the back side panels is stretchable in a direction substantially parallel to the substantially parallel portions of the waist end and leg end edges.

49. The absorbent pant garment of claim 27, wherein each of the back side panels is stretchable in a direction substantially non-parallel to the substantially parallel portions of the waist end and leg end edges.

50. The absorbent pant garment of claim 27, wherein each of the back side panels is stretchable in multiple directions.

51. The absorbent pant garment of claim 27, wherein the outer cover forms part of a laminate that comprises the front and back side panels.

52. An absorbent pant garment, comprising:
an absorbent chassis defining a waist opening and first and second leg openings;
a first front side panel and a first back side panel forming a refastenable seam there between, wherein the first refastenable seam is refastenable from the waist opening to the first leg opening, wherein the first front side panel and the first back side panel each has a waist end edge, a distal edge, and a leg end edge, the first front side panel and the first back side panel each being elastomeric along the leg end edge, wherein a portion of the waist end edge and a portion of the leg end edge of each panel is substantially parallel to one another adjacent the distal edge, the first front side panel includes a first fastening component bonded to a first surface of the first front side panel adjacent to a distal edge of the first front side panel between the parallel portions of the waist end edge and the leg end edge, and the first back side panel includes a first mating fastening component bonded to a second surface of the first back side panel adjacent to a distal edge of the first back side panel between the parallel portions of the waist end edge and the leg end edge, wherein the second surface is opposite the first surface and the first fastening component is refastenably connected to the first mating fastening component, one of the first fastening component and the first mating fastening component being a smaller fastening component of the first refastenable seam, the parallel portions of the waist end edge and the leg end edge each having a length greater than a transverse width of the smaller fastening component of the first refastenable seam; and a second front side panel and a second back side panel forming a second refastenable seam there between, wherein the second refastenable seam is refastenable from the waist opening to the second leg opening, wherein the second front side panel and the second back side panel each has a waist end edge, a distal edge, and a leg end edge, the second front side panel and the second back side panel each being elastomeric along the leg end edge, wherein a portion of the waist end edge and a portion of the leg end edge of each panel is substantially parallel to one another adjacent the distal edge, the second front side panel includes a second fastening component bonded to a first surface of the second front side panel adjacent to a distal edge of the second front side panel between the parallel portions of the waist end edge and the leg end edge, and the second back side panel includes a second mating fastening component bonded to a second surface of the second back side panel adjacent to a distal edge of the second back side panel between the parallel portions of the waist end edge and the leg end edge, wherein the second surface is opposite the first surface and the second fastening component is refastenably connected to the second mating fastening component, one of the second fastening component and the second mating fastening component being a smaller fastening component of the second refastenable seam, the parallel portions of the waist end edge and the leg end edge each having a length greater than a transverse width of the smaller fastening component of the second refastenable seam; and wherein the absorbent chassis has an outer cover that forms the first and second front and back side panels to create a one-piece garment exterior.

53. The absorbent pant garment of claim 52, wherein the first refastenable seam includes a transverse overlap wider than a transverse width of the smaller fastening component of the first refastenable seam, and the second refastenable seam includes a transverse overlap wider than a transverse width of the smaller fastening component of the second refastenable seam.

54. The absorbent pant garment of claim 52, wherein the portion of the waist end edge and the portion of the leg end edge of each of the first and second back side panels are substantially parallel to one another adjacent the distal edge for a distance of at least 1.2 times the transverse width of the smaller fastening component of the corresponding refastenable seam.

55. The absorbent pant garment of claim 52, wherein the portion of the waist end edge and the portion of the leg end edge of each of the first and second back side panels are substantially parallel to one another adjacent the distal edge for a distance of at least 1.5 times the transverse width of the smaller fastening component of the corresponding refastenable seam.

56. The absorbent pant garment of claim 52, wherein the portion of the waist end edge and the portion of the leg end edge of each of the first and second front side panels are substantially parallel to one another adjacent the distal edge for a distance of at least 1.2 times the transverse width of the smaller fastening component of the corresponding refastenable seam.

57. The absorbent pant garment of claim 52, wherein the portion of the waist end edge and the portion of the leg end edge of each of the first and second front side panels are substantially parallel to one another adjacent the distal edge for a distance of at least 1.5 times the transverse width of the smaller fastening component of the corresponding refastenable seam.

58. The absorbent pant garment of claim 52, wherein the first fastening component is integral with the first front side panel and the second fastening component is integral with the second front side panel.

59. The absorbent pant garment of claim 52, wherein the first mating fastening component is integral with the first back side panel and the second mating fastening component is integral with the second back side panel.

60. The absorbent pant garment of claim 52, wherein the first fastening component is bonded to the first front side panel and the second fastening component is bonded to the second front side panel.

61. The absorbent pant garment of claim 52, wherein the first mating fastening component is bonded to the first back side panel and the second mating fastening component is bonded to the second back side panel.

62. The absorbent pant garment of claim 52, wherein the first fastening component is bonded to and extends past the distal edge of the first front side panel of the second fastening component is bonded to and extends past the distal edge of the second front side panel.

63. The absorbent pant garment of claim 52, wherein the first mating fastening component is bonded to and extends past the distal edge of the first back side panel and the second mating fastening component is bonded to and extends past the distal edge of the second back side panel.

64. The absorbent pant garment of claim 52, wherein the leg end edge of each of the first and second back side panels further comprises a portion transversely offset from the first and second mating fastening components that is non-parallel and non-perpendicular to the waist end edge of each of the first and second back side panels.

65. The absorbent pant garment of claim 52, wherein the leg end edge of each of the first and second front side panels further comprises a portion transversely offset from the first and second fastening components that is non-parallel and non-perpendicular to the waist end edge of each of the first and second front side panels.

66. The absorbent pant garment of claim 52, wherein each of the side panels is permanently attached to the outer cover of the absorbent chassis along an attachment edge opposite the distal edge of each side panel.

67. The absorbent pant garment of claim 52, wherein each of the side panels is continuous with a layer of the absorbent chassis.

68. The absorbent pant garment of claim 52, wherein each of the front side panels comprises a stretch-bonded laminate.

69. The absorbent pant garment of claim 52, wherein each of the back side panels comprises a stretch-bonded laminate.

70. The absorbent pant garment of claim 52, wherein each of the front side panels comprises a plurality of elastic strands adjacent the leg end edge.

71. The absorbent pant garment of claim 52, wherein each of the back side panels comprises a plurality of elastic strands adjacent the leg end edge.

72. The absorbent pant garment of claim 52, wherein the distal edge of each of the first and second back side panels is perpendicular to the portion of the waist end edge and the portion of the leg end edge that are substantially parallel to one another.

73. The absorbent pant garment of claim 52, wherein the distal edge of each of the first and second back side panels is non-perpendicular to the portion of the waist end edge and the portion of the leg end edge that are substantially parallel to one another.

74. The absorbent pant garment of claim 52, wherein the distal edge of each of the first and second front side panels is perpendicular to the portion of the waist end edge and the portion of the leg end edge that are substantially parallel to one another.

75. The absorbent pant garment of claim 52, wherein the distal edge of each of the first and second front side panels is non-perpendicular to the portion of the waist end edge and the portion of the leg end edge that are substantially parallel to one another.

76. The absorbent pant garment of claim 52, wherein the outer cover forms part of a laminate that comprises the front and back side panels.

* * * * *